(12) United States Patent
Masaki

(10) Patent No.: US 9,662,121 B2
(45) Date of Patent: May 30, 2017

(54) SIMPLE AUTO ELECTRONIC TOURNIQUET

(71) Applicant: Nobuyuki Masaki, Chiba (JP)

(72) Inventor: Nobuyuki Masaki, Chiba (JP)

( * ) Notice: Subject to any disclaimer, the term of this patent is extended or adjusted under 35 U.S.C. 154(b) by 122 days.

(21) Appl. No.: 14/363,583

(22) PCT Filed: Dec. 5, 2012

(86) PCT No.: PCT/JP2012/081457
§ 371 (c)(1),
(2) Date: Jun. 6, 2014

(87) PCT Pub. No.: WO2013/084912
PCT Pub. Date: Jun. 13, 2013

(65) Prior Publication Data
US 2014/0336697 A1 Nov. 13, 2014

(30) Foreign Application Priority Data

Jul. 12, 2011 (JP) .................................. 2011-267873

(51) Int. Cl.
*A61B 17/135* (2006.01)
*A61B 17/132* (2006.01)
(Continued)

(52) U.S. Cl.
CPC ........ *A61B 17/1355* (2013.01); *A61B 5/0225* (2013.01); *A61B 5/02233* (2013.01);
(Continued)

(58) Field of Classification Search
CPC . A61B 17/1355; A61B 17/132; A61B 17/135; A61B 17/1322; A61B 5/68;
(Continued)

(56) References Cited

U.S. PATENT DOCUMENTS 3,847,142 A * 11/1974 Williams, Jr. ......... A61B 5/026
600/507
4,134,396 A * 1/1979 Doll ..................... A61B 5/0265
600/504
(Continued)

FOREIGN PATENT DOCUMENTS

JP 64-80342 A 3/1989
JP 2009-95516 A 5/2009

OTHER PUBLICATIONS

International Search Report of PCT/JP2012/081457, dated Mar. 12, 2013.

*Primary Examiner* — Christopher L Templeton
(74) *Attorney, Agent, or Firm* — Sughrue Mion, PLLC

(57) ABSTRACT

The present invention provides a simple auto electronic tourniquet which does not inflict pain on a person receiving the tourniquet in a preparatory stage before venipuncture and which shortens the time required in preparation for venipuncture. The simple auto electronic tourniquet includes a manchette (wrapping member) wrapped around an upper arm and a controller provided on the manchette for controlling pressures to the upper arm by the wrapping member. The controller includes a diastolic blood pressure detecting circuit and a pressure setting and maintenance circuit. The pressure setting and maintenance circuit setting pressures of the manchette at a time when changes of a biological signal are detected by the diastolic blood pressure detecting circuit as target pressures.

9 Claims, 6 Drawing Sheets

(51) Int. Cl.
*A61M 5/172* (2006.01)
*A61M 5/42* (2006.01)
*A61B 5/00* (2006.01)
*A61B 5/022* (2006.01)
*A61B 5/0225* (2006.01)

(52) U.S. Cl.
CPC .......... *A61B 5/6843* (2013.01); *A61B 17/135* (2013.01); *A61M 5/1723* (2013.01); *A61M 5/42* (2013.01); *A61B 17/132* (2013.01); *A61B 17/1322* (2013.01)

(58) Field of Classification Search
CPC ......... A61B 5/6843; A61B 5/72; A61B 5/022; A61B 5/0225; A61B 5/024; A61B 5/02438; A61B 5/02444
See application file for complete search history.

(56) References Cited

U.S. PATENT DOCUMENTS

| | | | | |
|---|---|---|---|---|
| 4,205,688 A * | 6/1980 | Hauser | ................. | A61B 5/0265 600/507 |
| 4,321,929 A * | 3/1982 | Lemelson | .......... | A61B 17/1355 600/301 |
| 4,479,494 A * | 10/1984 | McEwen | ........... | A61B 5/02141 600/495 |
| 4,548,198 A * | 10/1985 | Manes | ............... | A61B 17/1355 606/202 |
| 4,671,290 A * | 6/1987 | Miller | ................ | A61B 5/02225 600/494 |
| 5,842,996 A * | 12/1998 | Gruenfeld | ............ | A61B 17/135 600/490 |
| 2010/0324429 A1* | 12/2010 | Leschinsky | ........ | A61B 5/02208 600/493 |

* cited by examiner

SIMPLE AUTO ELECTRONIC TOURNIQUET

CROSS REFERENCE TO RELATED APPLICATIONS

This application is a National Stage of International Application No. PCT/JP2012/081457 filed Dec. 5, 2012, claiming priority based on Japanese Patent Application No. 2011-267873, filed Dec. 7, 2011, the contents of all of which are incorporated herein by reference in their entirety.

FIELD OF THE INVENTION

The present invention relates to a simple auto electronic tourniquet which can appropriately and easily perform venipuncture, drawing blood, securing of vein root (vascular security) and so on.

BACKGROUND ART

Tourniquet is usually performed in the sites such as the drawing blood by, for example, winding an elastic band around the arm of human body. However, nurses and so on conventionally depend on their own sense and decide constricting strength of the rubber band by themselves. Therefore, constricting strength is either too weak or too strong, and it is difficult to constrict the arm with appropriate tourniquet pressures. Therefore, the development of the simple auto electronic tourniquet which can automatically constrict the arm with appropriate tourniquet pressures has been expected.

On the other hand, as a tourniquet which could automatically perform tourniquet to some extent, the one has been known which comprises a manchette mountable to the arm of the human body, a pressure-applying means pressurizing the manchette, and a blood pressure measuring means for measuring the systolic blood pressure (maximum blood pressure) and the diastolic blood pressure (minimum blood pressure) of the person who mounted the manchette by either pressurizing or depressurizing the manchette with the pressure-applying means. The tourniquet is configured to perform tourniquet by measuring the diastolic blood pressure and the systolic blood pressure with the blood pressure measuring means and by setting pressures of the manchette between the diastolic blood pressure and the systolic blood pressure (e.g., reference cited 1).

In the tourniquet configured in such a way, the manchette is mounted to the arm first, and then the manchette is pressurized to pressures higher than the expected systolic blood pressure and is gradually depressurized. In the depressurizing process, the diastolic blood pressure and the systolic blood pressure are measured based on changes of the biological signal.

That is, in the depressurizing process, since developments of the Korotkov's sound, for example, as changes of the biological signal are detected, the systolic blood pressure is measured with pressures of the manchette at the time of detection. By continuing depressurizing, since disappearances of the Korotkov's sound are detected next, the diastolic blood pressure is measured with pressures of the manchette at the time of detection of disappearances. After that, the manchette is pressurized again, and pressures of the manchette are set in predetermined pressures between the diastolic blood pressure and the systolic blood pressure, by which tourniquet is performed.

By performing tourniquet in the above-described way, while the arterial blood flow is maintained, the venous blood flow is suspended and the vein is made dilated surely, by which venipuncture can be performed easily.

However, when the systolic blood pressure is detected with using the above-mentioned tourniquet, as the arm must be pressed in a pressure well beyond the systolic blood pressure, a problem is that pain is felt in the arm on the occasion. Besides, both of the systolic blood pressure and the diastolic blood pressure are measured, and then pressures of the manchette are set in a predetermined pressure between the systolic blood pressure and the diastolic blood pressure. Therefore, another problem is that much time is needed in the preparatory stage before venipuncture.

PRIOR ART DOCUMENTS

Patent Documents

[Patent Document 1]
JP 2009-95516

SUMMARY OF THE INVENTION

Problem to be Solved by the Invention

The present invention has been made in view of the above-mentioned circumstances. The object of the present invention is to provide a simple auto electronic tourniquet which does not inflict pain on a person receiving tourniquet in the preparatory stage before venipuncture and which shorten the time required in preparation for venipuncture.

Means to Solve the Problem

According to a first aspect of the present invention, a simple auto electronic tourniquet comprises a wrapping member wrapped around any of the extremities of the human body and a controller provided on the wrapping member and controlling pressures applied to the extremity by the wrapping member. The controller comprises a diastolic blood pressure detecting circuit and a pressure setting and maintenance circuit. The diastolic blood pressure detecting circuit detects changes of the biological signal concerning the diastolic blood pressure occurring in the extremity by controlling increase and decrease of pressures within the wrapping member. The pressure setting and maintenance circuit sets the pressures of the wrapping member at the time when changes of the biological signal are detected by the diastolic blood pressure detecting circuit as target pressures. Furthermore, the pressure setting and maintenance circuit controls the wrapping member so as to make its pressures fall within the range similar to the target pressures.

According to a second aspect of the present invention, in the first aspect thereof, the pressure setting and maintenance circuit sets maximum pressures by adding predetermined allowable pressures to the target pressures, sets minimum pressures by reducing predetermined allowable pressures more than 0 (zero) from the target pressures, and thereby controls the wrapping member so as to make its pressures fall within the range similar to the target pressures by actively increasing and decreasing its pressures. Also, when the pressure setting and maintenance circuit detects changes of the biological signal concerning the diastolic blood pressure occurring in the extremity in the pressure increase process, it sets the pressures of the wrapping member at the time of detection as target pressures and sets maximum pressures by adding predetermined allowable pressures to the target pressures. Further, when the pressure setting and maintenance circuit detects changes of the biological signal concerning the diastolic blood pressure occurring in the extremity in the pressure decrease process, it sets the pressures of the wrapping member at the time of detection as target pressures and sets minimum pressures by reducing predetermined allowable pressures more than 0 (zero) from the target pressures. Thereby, the pressure setting and maintenance circuit resets the target pressures, the maximum pressures and the minimum pressures depending on changes of the diastolic blood pressure.

According to a third aspect of the present invention, in the first or the second aspect thereof, the controller comprises a pressure switching decision circuit for determining to control not by the pressure setting and maintenance circuit but by a higher pressure setting and maintenance circuit in a case where pressures of the wrapping member are lower than predetermined pressures at the time when the diastolic blood pressure detecting circuit detects changes of the biological signal. The higher pressure setting and maintenance circuit detects changes of the biological signal occurring in the extremity by controlling so as to further increase pressures of the wrapping member at the time when the diastolic blood pressure detecting circuit detects changes of the biological signal, sets higher target pressures by reducing predetermined pressures from the pressures of the wrapping member at the time of detection, sets higher maximum pressure by adding predetermined allowable pressures to the higher target pressures, and sets higher minimum pressures by reducing predetermined allowable pressures more than 0 (zero) from the higher target pressures. When pressures of the wrapping member reach the higher maximum pressures, the higher pressure setting and maintenance circuit controls the wrapping member so as for its pressures to decrease, and when pressures of the wrapping member reach the higher minimum pressures, the higher pressure setting and maintenance circuit controls the wrapping member so as for its pressures to increase. Thereby, pressures of the wrapping member are maintained to the vicinities of the higher target pressures.

According to a fourth aspect of the present invention, in either one among the first to third aspects thereof, the controller comprises a venipuncturability informing circuit, which, after a predetermined time from the point when a target pressure is set for the first time, outputs to a informing means a signal informing of venipuncture being possible According to a fifth aspect of the present invention, in either one among the first to fourth aspects thereof, the controller comprises a tourniquet pressure abnormal informing circuit, which detects that pressures of the wrapping member become either higher than predetermined maximum management pressures or lower than predetermined minimum management pressures, and outputs to the informing means signals informing of tourniquet pressures being abnormal.

According to a sixth aspect of the present invention, in either one among the first to fifth aspects thereof, the controller comprises an allowed tourniquet time expiration informing circuit, which starts measuring tourniquet times from the points when the first target pressures are set and which outputs signals informing that tourniquet times reach predetermined allowable tourniquet times to the informing means at the time of their reaching.

According to a seventh aspect of the present invention, in either one among the first to sixth aspects thereof, the controller comprises a tourniquet discontinuance decision circuit, which shifts to a tourniquet discontinuance circuit in a case that changes of the biological signal cannot be detected by the diastolic blood pressure detecting circuit until pressures of the wrapping member reach predetermined pressures. The tourniquet discontinuance circuit controls so as to decrease in pressures of the wrapping member and outputs signals informing of tourniquet being impossible to the informing means.

According to an eighth aspect of the present invention, in either one among the first to seventh aspects thereof, the controller comprises a tourniquet release circuit reducing pressures of the wrapping member based on signals emitted from a tourniquet release button. Further, the tourniquet release button is provided on a casing which covers the controller and/or is movably provided from the casing, and emits the signals to the tourniquet release circuit.

According to a ninth aspect of the present invention, in either one among the first to eighth aspects thereof, the wrapping member comprises an air pump, a pressure control valve, a pressure sensor and a biological signal detecting sensor. The air pomp is a source of supply of the compressed air for obtaining pressures of the wrapping member. The pressure control valve adjusts pressures of the wrapping member by adjusting pressures of the air supplied from the air pump based on the command from the controller. The pressure sensor detects pressures of the wrapping member by pressures of the air within the wrapping member. The biological signal detecting sensor detects the biological signal.

According to a tenth aspect of the present invention, in the ninth aspects thereof, a fixed or variable flow-regulating valve is provided for adjusting decreasing speed of pressures within the wrapping member by limiting a rate of flow of the air discharged from the wrapping member.

Effects of the Invention

According to first aspect of the present invention, the diastolic blood pressure detecting circuit is provided for detecting changes of the biological signal concerning the diastolic blood pressure occurring in the extremity by controlling increase and decrease of pressures within the wrapping member. Further, the pressure setting and maintenance circuit is provided for setting the pressures of the wrapping member at the time when changes of the biological signal are detected by the diastolic blood pressure detecting circuit as target pressures and for controlling the wrapping member so as to make pressures of the wrapping member fall within the range similar to the target pressures. Therefore, pressures beyond the systolic blood pressure are not applied to any of the extremities (e.g., an upper arm) of the human body.

That is, changes of the biological signal concerning the diastolic blood pressure can be detected as developments of the Korotkov's sound, for example, in the process of gradually increasing in pressures of the wrapping member from approximately 0 (zero). Also, changes of the biological signal can be detected as disappearances of the Korotkov's sound in a process where pressures of the wrapping member are set so as to correspond to both of the blood pressure higher than the generally expected diastolic blood pressure and the blood pressure lower than the generally expected systolic blood pressure and the pressures of the wrapping member are gradually decreased. At all events, since the extremity such as the upper arms is not constricted by pressures higher than the systolic blood pressure in a process where the biological signal is detected and target pressures are set, the person who receives tourniquet is not inflicted in a preparatory phase before the venipuncture.

Besides, tourniquets can be performed by detecting changes of the biological signal concerning the diastolic blood pressure in a process for controlling increase and decrease in pressures of the wrapping member, by setting the pressures of the wrapping member at the time of detection as target pressures, and by controlling pressures of the wrapping member so as to fall in the range similar to the target pressures. Therefore, the time required for performing tourniquet can be shortened compared to the conventional technique where both the systolic blood pressure and the diastolic blood pressure are measured first and then pressures of the manchette are set therebetween.

Also, since tourniquets are performed either in the diastolic blood pressure or in the similar pressures, intravenous blood flow can be interrupted while arterial blood flow is maintained. Thus, there is an advantage that the vein is made dilated in a short time.

According to the second aspect of the present invention, the pressure setting and maintenance circuit sets target pressures with respect to both maximum pressures and minimum pressures, maintains pressures of the wrapping member to the vicinities of the target pressures by actively increasing or decreasing its pressures, resets the target pressures and the maximum pressures in the process of increasing pressures of the wrapping member, and resets the target pressures and the minimum pressure in the process of decreasing pressures of the wrapping member. Therefore, since the diastolic blood pressure of a person receiving tourniquet changes, pressures of the wrapping member can be controlled to follow the change.

Therefore, if the diastolic blood pressure temporarily increases and then gradually decreases for a mental tension at the venipuncture, for example, or if the diastolic blood pressure increases and decreases for some reasons, tourniquets can be easily performed with appropriate pressures which correspond to changes of the diastolic blood pressure.

According to the invention of claim 3, the pressure switching decision circuit is provided for determining to control not by the pressure setting and maintenance circuit but by the higher pressure setting and maintenance circuit in a case where pressures of the wrapping member are lower than predetermined pressure at the time when the diastolic blood pressure detecting circuit detects changes of the biological signal. The higher pressure setting and maintenance circuit detects changes of the biological signal by increasing pressures of the wrapping member, sets higher target pressures by reducing predetermined pressure from the pressure of the wrapping member at the time of the detection, sets higher maximum pressures and higher minimum pressures with respect to the higher target pressures, and controls pressures of the wrapping member so as for the pressures to fall between the higher maximum pressure and the higher minimum pressure, and thereby maintains the pressures thereof to the vicinities of the higher target pressure. Therefore, if pressures of the wrapping member corresponding to the diastolic blood pressure show abnormally low value, tourniquets can be performed safely with pressures higher than the pressures of the wrapping member and lower than the systolic blood pressure.

Also, since pressures of the wrapping member does not increase higher than the systolic blood pressure at the time when higher target pressures are set, persons receiving tourniquet can be prevented from feeling pain by pressures of the wrapping member. Also, pressures of the wrapping member corresponding to the systolic blood pressure are detected, and higher target pressures are set by reducing predetermined pressures from the pressures of the wrapping member detected. Therefore, venipuncture can be prepared in a shorter time than the conventional case.

According to the fourth aspect of the present invention, since the venipuncturability informing circuit is provided for outputting a signal informing of venipuncture being possible to the informing means after a predetermined time from the point when a target pressure is set for the first time, nurses and so on who receive the information can confirm veins after loaded with blood and dilated. Besides, there is an advantage that nurses and so on can devote themselves to other work such as sterilizing a puncturing portion of the human body after attaching a simple automatic electronic tourniquet of the present invention to either extremity of the human body.

According to the fifth aspect of the present invention, since the tourniquet pressure abnormal informing circuit is provided for detecting that pressures of the wrapping member become either higher than predetermined maximum management pressures or lower than minimum management pressures, and outputting to the informing means signals informing of tourniquet pressures being abnormal, it is possible to cope with such abnormal tourniquet pressures immediately.

According to the sixth aspect of the present invention, since the allowed tourniquet time expiration informing circuit is provided for starting measuring tourniquet times from the points when the first target pressures are set, and for outputting signals informing that tourniquet times reach predetermined allowable tourniquet times to the informing means at the time of their reaching. Therefore, ill-effects on such as the upper arm due to tourniquets can be prevented from occurring.

According to the seventh aspect of the present invention, the tourniquet discontinuance decision circuit is provided, which shifts to the tourniquet discontinuance circuit in a case that changes of the biological signal cannot be detected by the diastolic blood pressure detecting circuit until pressures of the wrapping member reach predetermined pressures. Further, the tourniquet discontinuance circuit controls so as to decrease pressures of the wrapping member and outputs signals informing of tourniquets being impossible to the informing means. Therefore, if abnormality occurs in which the diastolic blood pressure cannot be detected, a safety measure is taken to decrease pressures of the wrapping member and the abnormality can be informed to nurses and so on.

According to the eighth aspect of the present invention, since the tourniquet release means and the tourniquet release circuit are provided, the tourniquet release means is operated after the vein routes for blood transfusion and drip infusion are secured, by which pressures of the wrapping member to which the tourniquet is conducted is released immediately.

Besides, if the tourniquet release means is movably provided in a position not restricted by the casing of the controller, since work for securing the vein route can be done by having the tourniquet release means at hand, pressures of the wrapping member can be released by promptly operating the tourniquet release means after the work is finished. Also, there is an advantage that if both hands are not usable for securing vein routes, the tourniquet release means can be operated by pushing with an elbow or by biting with teeth, for example.

According to the ninth aspect of the present invention, since the wrapping member is provided with at least the air pump, the pressure control valve, the pressure sensor and the biological signal detecting sensor, developments of such as the Korotkov's sound can be detected by the biological signal detecting sensor at a pressure at some stage by gradually increasing the setting pressure of the pressure control valve at predetermined intervals. Also, conversely, disappearances of the Korotkov's sound can be detected by the biological signal sensing sensor at a pressure at some stage by gradually decreasing the setting pressure of the pressure control valve at predetermined intervals.

Furthermore, when the pressures become constant at their each stage, air flow in the pressure control valve stops and the fluid sound due to the air flow disappears, by which presence and absence of the Korotkov's sound can be surely detected by the biological signal detecting sensor. That is, changes of the biological signal can be surely detected by biological signal detecting sensor. Also, increasing speed and decreasing speed of the pressure can be adjusted by adjusting the interval.

According to the tenth aspect of the present invention, since the fixed or variable flow-regulating valve is provided for adjusting a rate of flow of the air exhausted from the wrapping member, decreasing speed of pressures of the wrapping member can be adjusted. Also, if the variable flow-regulating valve is provided, time to reach the minimum pressure from the maximum pressure can be changed freely by adjusting a rate of passing flow by the electric signals or by manual operation.

EMBODIMENT OF THE PRESENT INVENTION

A form to perform the present invention is described based on an example in detail.

Embodiment 1

Figure 1:
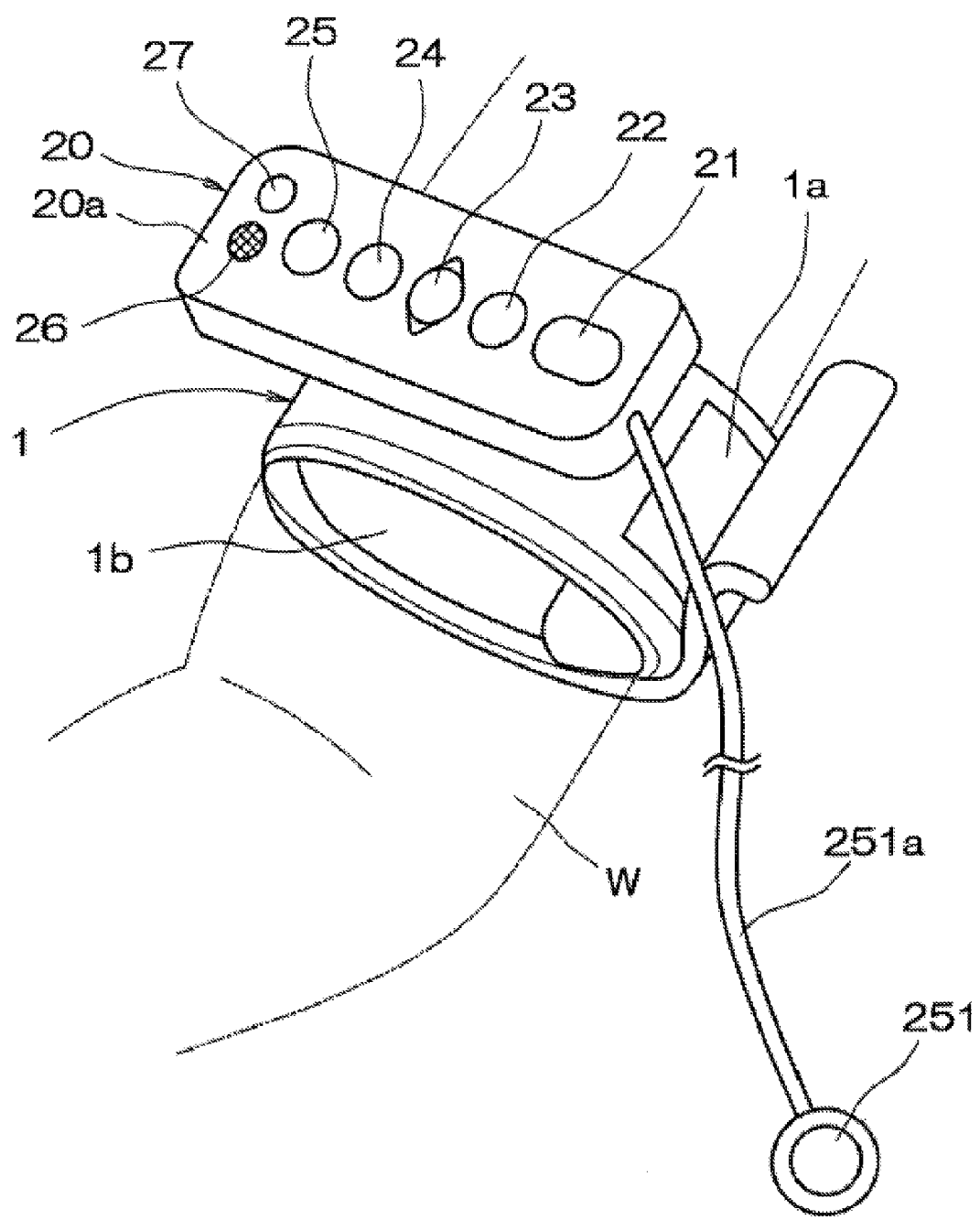
FIG. 1 is a perspective diagram which shows the appearance of a simple automatic electronic tourniquet shown as the first embodiment of the present invention.
Figure 2:
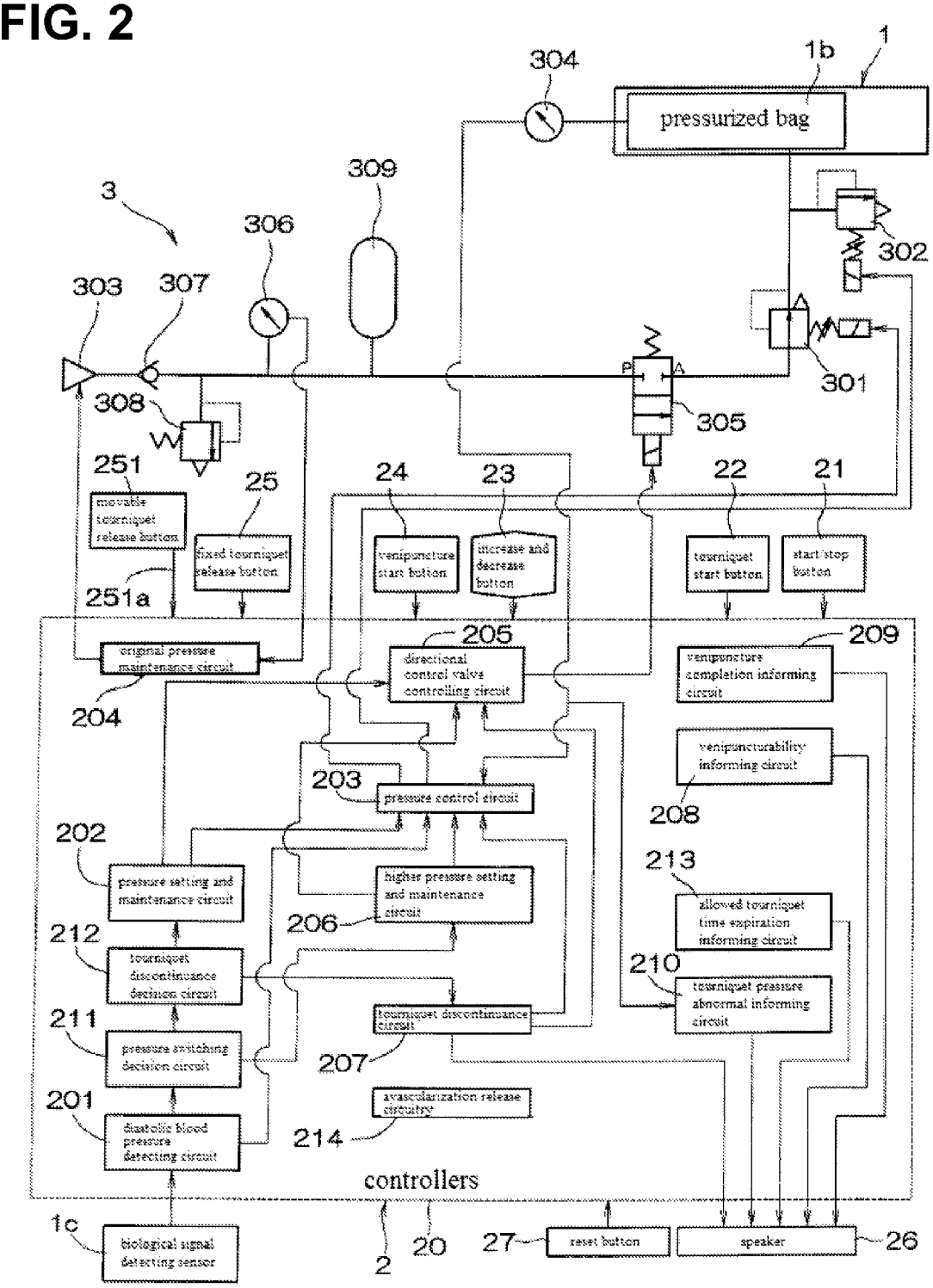
FIG. 2 is a block diagram to show the controllers in a simple automatic electronic tourniquet shown as the first embodiment of the present invention.

The first embodiment of the present invention for a simple automatic electronic tourniquet of the present invention as shown in FIGS. 1 and 2 comprises a manchette (wrapping member) 1 mounted so as to be wrapped around the upper arm W, one of the extremities of the human body, and a controller 2 integrally provided on the manchette 1.

When wrapped around the upper arm W, the manchette 1 is maintained in a roll-like shape by a surface-formed fastener part 1a, and is either attachable to or detachable from the upper arm W easily.

Also, the manchette 1 comprises a pressurized bag 1b at its inner surface when rolled for applying pressure to the upper arm W.

At a portion of either the manchette 1 or the pressurized bag 1b which contacts with the upper arm W, a biological signal detecting sensor 1c (cf. FIG. 2) for detecting the biological signal such as Korotkov's sound which either develops or disappears depending on the condition of intra-arterial blood flow.

Controller 2 comprises an electronic device having hardware resources with the computer, into which circuits are incorporated for controlling by implementing software of the sequence program. And since the controller 2 in this example, as shown in FIG. 2, controls pressures of the manchette 1 to the upper arm W by controlling pressure of the air supplied to the pressurized bag 1b through a pneumatic equipment 3, it further comprises a diastolic blood pressure detecting circuit 201 and a pressure setting and maintenance circuit 202.

The diastolic blood pressure detecting circuit 201 controls a directional control valve 305 of the pneumatic equipment 3 through a directional control valve controlling circuit 205 provided in the controller 2, and also controls a reducing valve (pressure control valve) 301 of the pneumatic equipment 3 and a relief valve (pressure control valve) 302 through a pressure control circuit 203 provided in the controller 2, by which it controls pressure of the air in pressurized bag 1b.

Thereby, the diastolic blood pressure detecting circuit 201 detects developments and disappearances of the Korotkov's sound as changes of the biological signal concerning the diastolic blood pressure occurring in the upper arm W by increasing or decreasing pressures of the manchette 1.

That is, the diastolic blood pressure detecting circuit 201 changes the directional control valve 305 through the directional control valve controlling circuit 205 in a condition where pressures of the pressurized bag 1b are approximately 0 (i.e., an atmospheric pressure) or lower than the diastolic blood pressure, and thereby makes its P port and A port communicable and possible for the compressed air from an air pump 303 of the pneumatic equipment 3 to be supplied to the side of the pressurized bag 1b. Then, the diastolic blood pressure detecting circuit 201 sets a relief valve 302 in predetermined pressures more than the diastolic blood pressure through the pressure control circuit 203 and then gradually increases pressures of the pressurized bag 1b by gradually increasing the setting pressure of the reducing valve 301 at pre-determined intervals, thereby gradually presses the upper arm and detects the development of the Korotkov's sound during the process by a biological signal detecting sensor 1c.

Note that the diastolic blood pressure detecting circuit 201 may be configured so as to detect disappearances of the Korotkov's sound in a process of gradually decreasing pressures of the pressurized bag in a case where pressures of the pressurized bag 1b are beyond the diastolic blood pressure. In this case, the diastolic blood pressure detecting circuit 201 sets the setting pressure of the reducing valve 301 to approximately 0 and thereby prevents the compressed air supplied from the air pump 303 from flowing into the side of the pressurized bag 1b through the reducing valve 301, then gradually decreasing the setting pressure of the relief valve 302 in predetermined intervals. Note that when decreasing the pressure of the pressurized bag 1b, communications between the P port and the A port are made suspended by returning the directional control valve 305 to the neutral position through the directional control valve controlling circuit 205, by which the compressed air may be prevented from flowing into the side of the pressurized bag 1b. In this case, the setting pressure of the reducing valve 301 may or may not be set to approximately 0.

When the pressure setting and maintenance circuit 202 detects either developments or disappearances of the Korotkov's sound by the diastolic blood pressure detecting circuit 201, it detects pressures of the pressurized bag 1b by the pressure sensor 304, thereby sets the pressures as target pressures, and also controls the reducing valve 301 and the relief valve 302 through the pressure control circuit 203 so as to make the pressures of the pressurized bag 1b fall within the range similar to the target pressures.

In this case, the pressure setting and maintenance circuit 202 sets maximum pressures by adding predetermined allowable pressures (allowable pressures) to the target pressures, sets minimum pressures by reducing predetermined allowable pressures more than 0 (zero) from the target pressures, and thereby controls pressures of the manchette 1 so as to make the pressures of the pressurized bag 1b fall within the range similar to the target pressure by actively increasing or decreasing pressures of the pressurized bag 1b through the reducing valve 301 and the relief valve 302, Furthermore, when the pressure setting and maintenance circuit 202 again detects developments of the Korotkov's sound occurring in the upper arm W in the pressure increase process of the pressurized bag 1b, it sets the pressures of the pressurized bag 1b at the time of detection as target pressures and sets maximum pressures by adding predetermined allowable pressures (allowable pressures) to the target pressures. Further, when the pressure setting and maintenance circuit 202 detects disappearances of the Korotkov's sound occurring in the upper arm W in the pressure decrease process of the pressurized bag 1b, it sets the pressures of the pressurized bag 1b at the time of detection as target pressures and sets minimum pressures by reducing predetermined allowable pressures more than 0 (zero) from the target pressures. Thereby, the pressure setting and maintenance circuit 202 resets the target pressures, the maximum pressures and the minimum pressures depending on changes of the diastolic blood pressure.

Note that the pressure setting and maintenance circuit 202 maintains the communication between the P port and the A port by controlling the directional control valve 305 through the directional control valve controlling circuit 205. However, when the pressure setting and maintenance circuit 202 decreases pressure of the pressurized bag 1b, it may switch the directional control valve 305 so as to make the communication between the P port and the A port suspended. In this case, as described above, the setting pressure of the reducing valve 301 may be or may not be controlled to be set to approximately 0 (zero).

Furthermore, the controller 2 comprises a pressure switching decision circuit 211 for determining to control not by the pressure setting and maintenance circuit 202 but by a higher pressure setting and maintenance circuit 206 in a case where pressures of the pressurized bag 1b are lower than predetermined pressures at the time when the diastolic blood pressure detecting circuit 201 detects change of the biological signal.

The higher pressure setting and maintenance circuit 206 detects disappearances of the Korotkov's sound concerning the systolic blood pressure occurring in the upper arm W by controlling so as to further increase pressures of the pressurized bag 1b at the time when changes of the biological signal are detected by the diastolic blood pressure detecting circuit 201, and sets higher target pressures by reducing predetermined pressures from the pressures of the pressurized bag 1b at the time of detection. Furthermore, the higher pressure setting and maintenance circuit 206 sets higher maximum pressures by adding predetermined allowable pressures to the higher target pressure, and sets higher minimum pressures by reducing predetermined allowable pressure more than 0 (zero) from the higher target pressure. And, when pressures of the pressurized bag 1b reach the higher maximum pressure, the higher pressure setting and maintenance circuit 206 controls the reducing valve 301 and the relief valve 302 through the pressure control circuit 203 so as for pressures of the pressurized bag 1b to decrease, and when pressures of the pressurized bag 1b reach the higher minimum pressure, the higher pressure setting and maintenance circuit 206 controls the reducing valve 301 and the relief valve 302 through the pressure control circuit 203 so as for pressures of the pressurized bag 1b to increase, and thereby maintains pressures of the pressurized bag 1b to the vicinities of the higher target pressures.

Also, the controller 2 comprises an original pressure maintenance circuit 204 for maintaining in a predetermined range the pressure of the air supplied from an air pump 303 and supplied from the directional control valve 305 to the pressurized bag 1b.

The original pressure maintenance circuit 204 takes control of start and stop of the air pump 303 so as for the pressure of the air supplied from the air pump 303 to fall within a predetermined range of pressure. That is, the original pressure maintenance circuit 204 controls so as to start the air pump 303 until a pressure sensor 306 provided on the discharge side of the air pump 303 detects 155 mmHg, for example, as the upper limit, controls so as to stop the air pump 303 when the pressure sensor 306 detects the pressure reaching to the upper limit, and controls so as to start the air pump 303 when the pressure detected by the pressure sensor 306 gradually decreases due to stopping of the air pump 303 to reach 145 mmHg, for example, as the lower limit. Thereby, the original pressure maintenance circuit 204 controls so as for the pressure of the air at the discharge side of the air pump 303 to fall within the range of 145-155 mmHg.

Also, near the discharge opening of the air pump 303, a check valve 307 is arranged for preventing the compressed air from flowing backward to the side of the air pump 303. Also, a relief valve 308, the pressure sensor 306, an accumulator 309, the directional control valve 305, the reducing valve 301 and the relief valve 302 are arranged sequentially.

By setting the relief valve 308 at 170 mmHg, for example, the pressure of the discharge side of the air pump 303 is configured to not exceed 170 mmHg in a case any failure occurs by any chance in the original pressure maintenance circuit 204 and so on, by which safety of the pneumatic circuitry 3 is ensured and adverse effects on the human body by the air pressure supplied to the pressurized bag 1b is prevented.

The accumulator 309 stabilizes a rate of flow of the air supplied to the pressurized bag 1b by saving the air supplied from the air pump 303.

Also, the controller 2 is covered by a casing 20, and its surface section 20a (cf. FIG. 1) is provided with a start/stop button 21. The start/stop button 21 is a kind of switch, which starts the electric power circuit (not illustrated in the FIGs) of the controller 2 by the first button-pushing operation and stops it by the second button-pushing operation. The original pressure maintenance circuit 204 starts controlling with the start of the electric power circuit. Therefore, when the air pump 303 starts with the pushing of the start/stop button 21, the circuit of the upstream of the directional control valve 305, the accumulator 309 and so on are loaded with the air discharged from the air pump 303 and its pressure is maintained in the aforementioned range of 145-155 mmHg.

Also, the surface section 20a of the casing 20 is provided with a tourniquet start button 22. This tourniquet start button 22 is also a kind of electric switch, and push of the tourniquet start button starts the diastolic blood pressure detecting circuit 201, the pressure setting and maintenance circuit 202, the pressure control circuit 203, the directional control valve controlling circuit 205, the pressure switching decision circuit 211, the higher pressure setting and maintenance circuit 206 and so on mentioned above as needed, so as to maintain pressures of the pressurized bag 1b in the range between the maximum pressures and the minimum pressures.

Also, the controller 2 comprises a venipuncturability informing circuit 208, which outputs a signal informing that venipuncture is possible to a speaker (informing means) 26 after a predetermined time (approximately ten seconds) from the point when a target pressure is set for the first time. Therefore, nurses and so on can notice with an alarm sound from the speaker 26 that venipuncture is possible. Also, the surface section 20a of the casing 20 is provided with a reset button 27 to stop the alarm sound from the speaker 26.

Note that if vein dilatation is not enough even after informing by the venipuncturability informing circuit 208, pressures of the pressurized bag 1b can be adjusted to either the increasing or decreasing direction by pushing a pressure increase-decrease button 23 provided on the surface section 20a of the casing 20. That is, the pressure increase-decrease button 23 controls the reducing valve 301 and the relief valve 302 through the pressure control circuit 203 based on either the increase or decrease signal from the pressure increase-decrease button 23 itself, and thereby manually controls increase and decrease of pressures of the pressurized bag 1b.

Also, the surface section 20a of the casing 20 is provided with a venipuncture start button 24 to push when venipuncture starts. The controller 2 comprises a venipuncture completion informing circuit 209, which starts measuring times based on a venipuncture start signal input by pushing the venipuncture start button 24, and outputs to the speaker 26 a signal informing that venipuncture times reach predetermined venipuncture times at the time of their reaching.

Furthermore, the controller 2 comprises an allowed tourniquet time expiration informing circuit 213, which starts measuring times from the point when the first target pressures are set, and outputs to the speaker 26 a signal informing that tourniquet times reach predetermined allowable tourniquet times at the time of their reaching.

Also, the controller 2 comprises a tourniquet pressure abnormal informing circuit 210, which detects through the pressure sensor 304 that pressures of the pressurized bag 1b as the pressures of manchette 1 become either higher than predetermined maximum management pressures or lower than predetermined minimum management pressures, and outputs to the speaker 26 signals informing of tourniquet pressures being abnormal.

Also, the controller 2 comprises a tourniquet discontinuance decision circuit 212, which shifts to a tourniquet discontinuance circuit 207 in a case that changes of the biological signal cannot be detected by the diastolic blood pressure detecting circuit 201 until pressures of the pressurized bag 1b reach predetermined pressures.

The tourniquet discontinuance circuit 207 controls so as to decrease pressures of the pressurized bag 1b and outputs to the speaker 26 signals informing of tourniquets being impossible. That is, the tourniquet discontinuance circuit 207 controls so as to suspend the communication between the P port and the A port of the directional control valve 305 through the directional control valve controlling circuit 205, and also controls so as to return the setting pressure of the reducing valve 301 and the relief valve 302 to 0 (zero) through the pressure control circuit 203.

Also, the casing 20 is provided with a fixed tourniquet release button (tourniquet release means) 25 on its surface section 20a and is also provided with a movable tourniquet release button (tourniquet release means) 251 through a signal line 251a. The movable tourniquet release button 251 is arranged on the front end of the signal line 251a which is flexible and movable without restricted by the casing 20.

Both the fixed tourniquet release button 25 and the movable tourniquet release button 251 are a kind of switch, and by pushing either button the tourniquet release signal is transmitted to a tourniquet release circuit 214 provided on the controller 2. The movable tourniquet release button 251 may be configured to transmit the tourniquet release signal to the tourniquet release circuit 214 wirelessly without using the signal line 251a.

Tourniquet release circuit 214 takes control of changing the P port and the A port of the directional control valve 305 so as to suspend the communication between both port through the directional control valve controlling circuit 205 based on the tourniquet release signal, also controls the reducing valve 301 and the relief valve 302 through the pressure control circuit 203, and thereby makes pressures of the pressurized bag 1b decrease rapidly to an atmospheric pressure. In this regard, in FIG. 2, the directional lines indicating the relations among the tourniquet release circuit 214, the pressure control circuit 203 and the directional control valve controlling circuit 205 are omitted.

According to the simple automatic electronic tourniquet configured as described above, tourniquet is performed on the upper arm W in pressures near the diastolic blood pressure without pressing the upper arm W at pressures more than the systolic blood pressure. Therefore, persons receiving a tourniquet are not inflicted in a preparatory phase before the venipuncture.

Besides, this simple automatic electronic tourniquet can make the time required for performing tourniquets shorter compared to the conventional technique where tourniquet are performed by measuring both systolic blood pressure and diastolic blood pressure and by setting pressures of the manchette therebetween.

Also, since tourniquets are performed either in the diastolic blood pressure or in the similar pressures, intravenous blood flow can be interrupted while the arterial blood flow is maintained. Thus, the vein is made dilated in a short time.

Furthermore, by pressure setting and maintenance circuit 202, the target pressures and the maximum pressures can be reset in the process of increase of pressures of the pressurized bag 1b, and the target pressures and the minimum pressures can also be reset in the process of decrease of pressures of the pressurized bag 1b. Therefore, if the diastolic blood pressure changes, pressures of the pressurized bag 1b can be controlled so as to follow the change.

Therefore, if the diastolic blood pressure temporarily increases and then gradually decreases for a mental tension at the venipuncture, for example, or if the diastolic blood pressure increases or decreases for some reasons, tourniquets can be easily performed with appropriate pressures which correspond to the post-change diastolic blood pressure.

Also, since the venipuncturability informing circuit 208 is provided for outputting a signal informing that venipuncture is possible to the speaker 26 after a predetermined time from the point when a target pressure is set for the first time, nurses and so on who receive the information can confirm that veins loaded enough with blood and dilated. Therefore, the nurses can perform venipuncture immediately after receiving the information. Besides, there is an advantage that the nurses can effectively use the time before receiving the information, to sterilize a puncturing portion of the human body and to do other work.

The tourniquet pressure abnormal informing circuit 210 is provided for detecting that pressures of the pressurized bag 1b becomes either higher than the predetermined maximum management pressures or lower than the minimum management pressures, and informing that tourniquet pressure is abnormal. Therefore, if abnormality occurs in the blood pressure during venipuncture, for example, it is possible to cope with it immediately.

Also, the venipuncture completion informing circuit 209 is provided for measuring time based on a venipuncture start signal input by operating the venipuncture start button 24, and for informing that venipuncture times reach predetermined venipuncture times. Therefore, the nurses can terminate venipuncture securely and safely at the most suitable time.

On the other hand, if pressures of the pressurized bag 1b are lower than predetermined pressures at the time when developments of the Korotkov's sound concerning the diastolic blood pressure are detected, to control by the higher pressure setting and maintenance circuit 206 is possible. Therefore, it is possible to perform tourniquets safely with pressures higher than the diastolic blood pressure and lower than the systolic blood pressure.

Also, if controlled by the higher pressure setting and maintenance circuit 206, pressures of the pressurized bag 1b does not increase to exceed the systolic blood pressure. Therefore, the person receiving tourniquet can be prevented from inflicted by pressures of the pressurized bag 1b. Also, the higher target pressures are set by detecting pressures of the pressurized bag 1b concerning the systolic blood pressure and by reducing predetermined pressures from pressures of the pressurized bag 1b. Therefore, venipuncture can be prepared in a short time compared with the conventional case.

Furthermore, the allowed tourniquet time expiration informing circuit 213 is provided for starting measuring times from the point when the first target pressures are set, and for outputting to the speaker 26 a signal informing that tourniquet times reach predetermined allowable tourniquet times at the time of their reaching. Therefore, ill-effects on the upper arm W due to tourniquets can be prevented from occurring.

Also, the fixed tourniquet release button 25, the movable tourniquet release button 215 and the tourniquet release circuit 214 are provided. Therefore, the fixed tourniquet release button 25 or the movable tourniquet release button 251 is operated after the vein routes for blood transfusion and drip infusion are secured, for example, by which pressures of the pressurized bag 1b with which tourniquet is performed are rapidly decreased so as to release the pressure of the manchette 1 immediately.

Besides, in a case of the movable tourniquet release button 251, since work for securing the vein routes can be done by having the movable tourniquet release button 251 at hand, pressures of the manchette 1 can be released by promptly operating the movable tourniquet release button 251 after the work is finished. Also, there is an advantage that if both hands are not usable for securing vein routes, the movable tourniquet release button 251 can be operated by pushing the button with an elbow or by biting the button with teeth, for example.

Also, the tourniquet discontinuance decision circuit 212 is provided, which shifts to the tourniquet discontinuance circuit 207 in a case that changes of the biological signal cannot be detected by the diastolic blood pressure detecting circuit 201 until pressures of the pressurized bag 1b reach predetermined pressures. The tourniquet discontinuance circuit 207 controls so as to decrease pressures of the pressurized bag 1b and also outputs to the speaker 26 signals informing of tourniquets being impossible. Therefore, if abnormality occurs in which the diastolic blood pressure cannot be detected, a safety measure is taken to decrease pressures of the pressurized bag 1b and the abnormality can be informed to nurses and so on. Accordingly, the nurses and so on can administer post-abnormality treatment more safely and immediately.

Furthermore, by gradually increasing the setting pressure of the reducing valve 301 at predetermined intervals, developments of such as the Korotkov's sound can be detected by the biological signal detecting sensor 1c at a pressure at some stage. Also, conversely, disappearances of the Korotkov's sound can be detected by the biological signal sensing sensor 1c at a pressure at some stage by gradually decreasing the setting pressure of the relief valve 302 at predetermined intervals.

And, when the pressures become constant at their each stage, air flow in the pressure control valve stops and the fluid sound due to the air flow disappears, by which presence and absence of the Korotkov's sound can be surely detected by the biological signal detecting sensor 1c.

Embodiment 2

Figure 3:
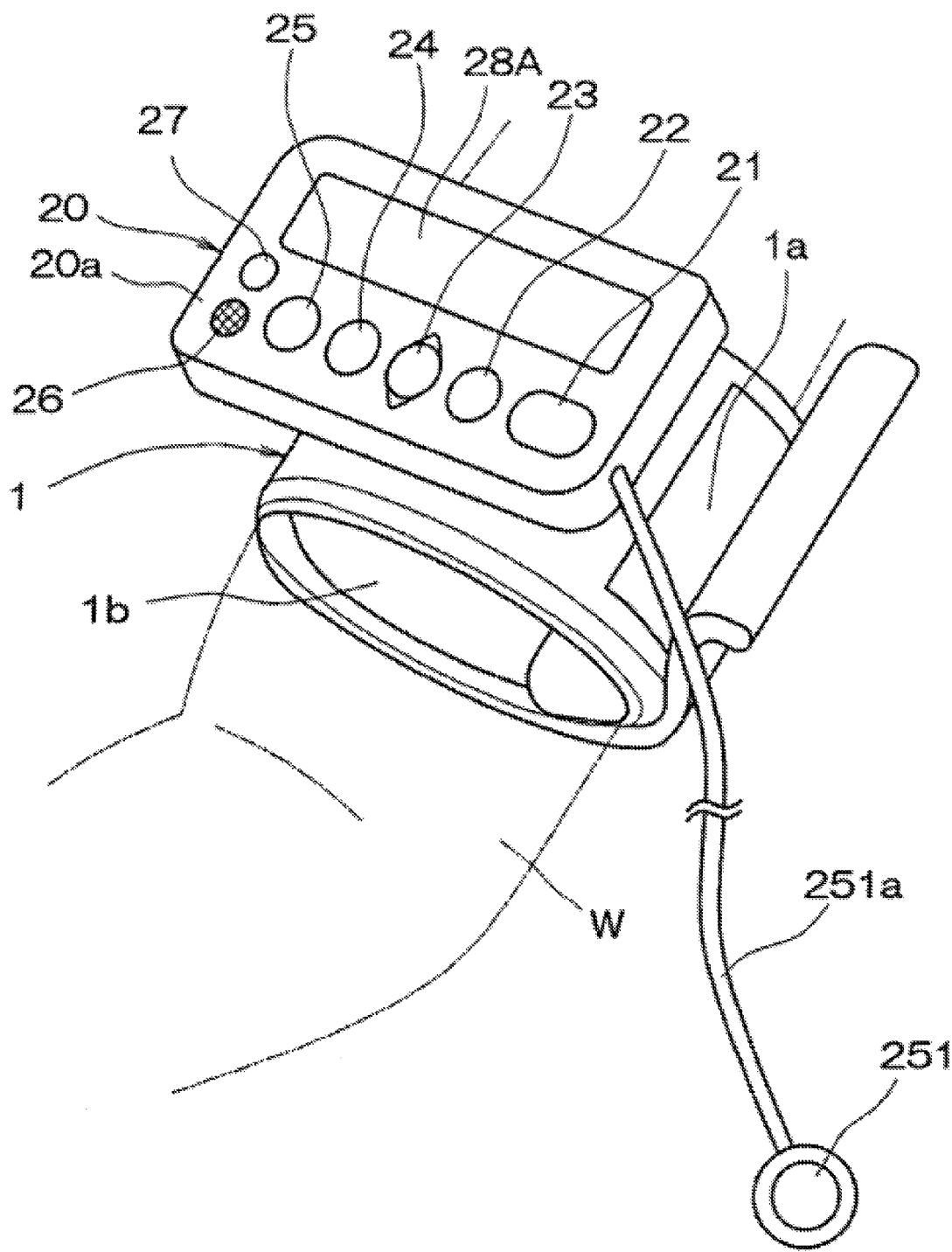
FIG. 3 is a perspective diagram which shows the appearance of a simple automatic electronic tourniquet shown as the second embodiment of the present invention.

Then, the second embodiment of the present invention is described with reference to FIGS. 3 and 4. However, the same code is referred to elements common to the elements of the first embodiment shown in FIGS. 1 and 2, and explanations thereon are omitted.

The difference between the second embodiment of the simple automatic electronic tourniquet and the first embodiment is that a small display 28A is provided as informing means besides the speaker 26, that a fixed throttle (fixed flow control valve) 305a is provided on the directional control valve 305, and that an exhaust directional control valve 310 for letting air out of the pressurized bag 1b rapidly.

Figure 4:
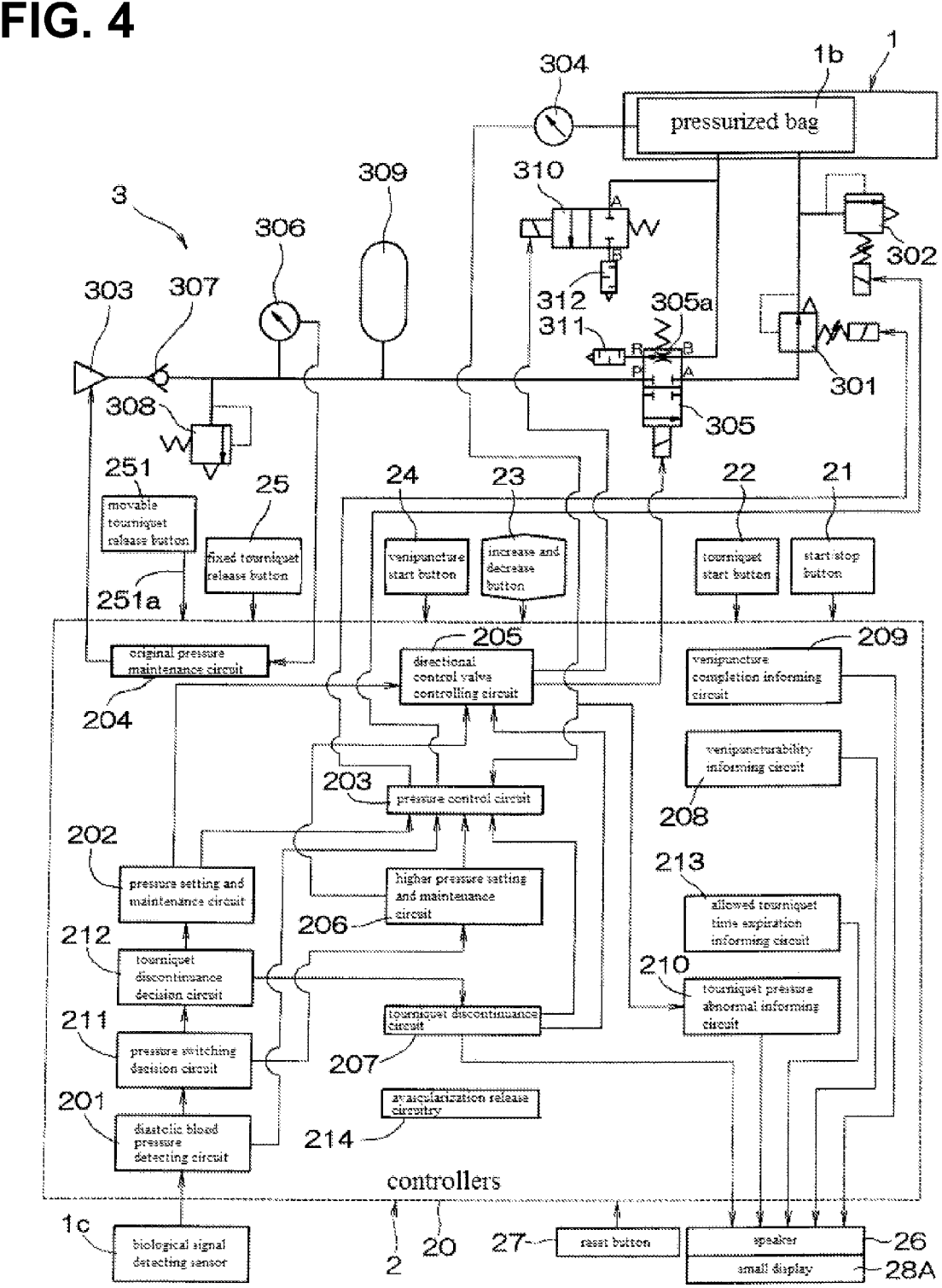
FIG. 4 is a block diagram which shows the controllers in a simple automatic electronic tourniquet shown as the second embodiment of the present invention.

That is, as shown in FIG. 4, when the directional control valve 305 is in the neutral position, the P port is not communicated with the A port, and the R port is communicated with the B port. The fixed throttle 305a is arranged between them. When switched, the P port is communicated with the A port, and the R port is not communicated with the B port. Also, the P port is connected to the side of the air pump 303, and the A port is connected to the side of the reducing valve 301. The R port is open to the atmosphere through a muffler 311, and the B port is connected to an exhaust port of the pressurized bag 1b.

When the exhaust directional control valve 310 is in the neutral position, the A port is not communicated with the B port. When switched, the A is communicated with the B port. Also, the A port is connected to both the exhaust port of the pressurized bag 1b and the B port of the directional control valve 305. The B port is open to the atmosphere through a muffler 312.

The fixed throttle 305a adjusts the decreasing speed of pressures of pressurized bag 1b by limiting a rate of flow of the air discharged from the pressurized bag 1b to the atmosphere.

The display 28A displays information contents and displays essential contents such as pressures of the pressurized bag 1b when pressures of the pressurized bag 1b is manually increased or decreased by using an increase and decrease button 23.

In the simple automatic electronic tourniquet configured as above-described, when pressures of the pressurized bag 1b are increased by the diastolic blood pressure detecting circuit 201, the pressure setting and maintenance circuit 202, the higher pressure setting and maintenance circuit 206, and so on, the directional control valve 305 is switched to make the P port of the directional control valve 305 communicated with the A port thereof, to make the R port of the directional control valve 305 not communicated with the B port thereof, and to make the A port of the exhaust directional control valve 310 not communicated with the B port thereof. Thereby, the air supplied from the air pump 303 flows into the pressurized bag 301 through the reducing valve 301, and pressures of the pressurized bag 1b is controlled by the reducing valve 301 and the relief valve 302.

On the other hand, when pressures of the pressurized bag 1b is decreased by the diastolic blood pressure detecting circuit 201, the pressure setting and maintenance circuit 202, the higher pressure setting and maintenance circuit 206, and so on, the air supply from the air pump 303 to the pressurized bag 1b is suspended by returning the directional control valve 305 to the neutral position through the directional control valve controlling circuit 205, and the pressurized bag 1b is also made open to the atmosphere through the fixed throttle 305a. Thereby, at the rate of airflow restricted by the fixed throttle 305a, pressures of the pressurized bag 1b can be decreased. Also, in this case, by controlling in order to maintain the exhaust directional control valve 310 in the neutral position through the directional control valve controlling circuit 205, the A port of the exhaust directional control valve 310 is cut off, and the air in the pressurized bag 1b is prevented from escaping from the exhaust directional control valve 310 to the atmosphere. Note that if the decreasing speed of pressures of pressurized bag 1b is controlled only by the fixed throttle 305a, the relief valve 302 can be omitted.

Also, when tourniquet is suspended or canceled by the tourniquet discontinuance circuit 207, the tourniquet release circuit 214, and so on, the air supply from the air pump 303 to the pressurized bag 1b is suspended by returning the directional control valve 305 to the neutral position through the directional control valve controlling circuit 205, and also the air in the pressurized bag 1b is discharged in large quantities to the atmosphere through the A port of the exhaust directional control valve 310, the B port thereof and the muffler 312 by switching the exhaust directional control valve 310 through the directional control valve controlling circuit 205. Thereby, pressures of the pressurized bag 1b are decreased to the atmospheric pressure momentarily.

Embodiment 3

Figure 5:
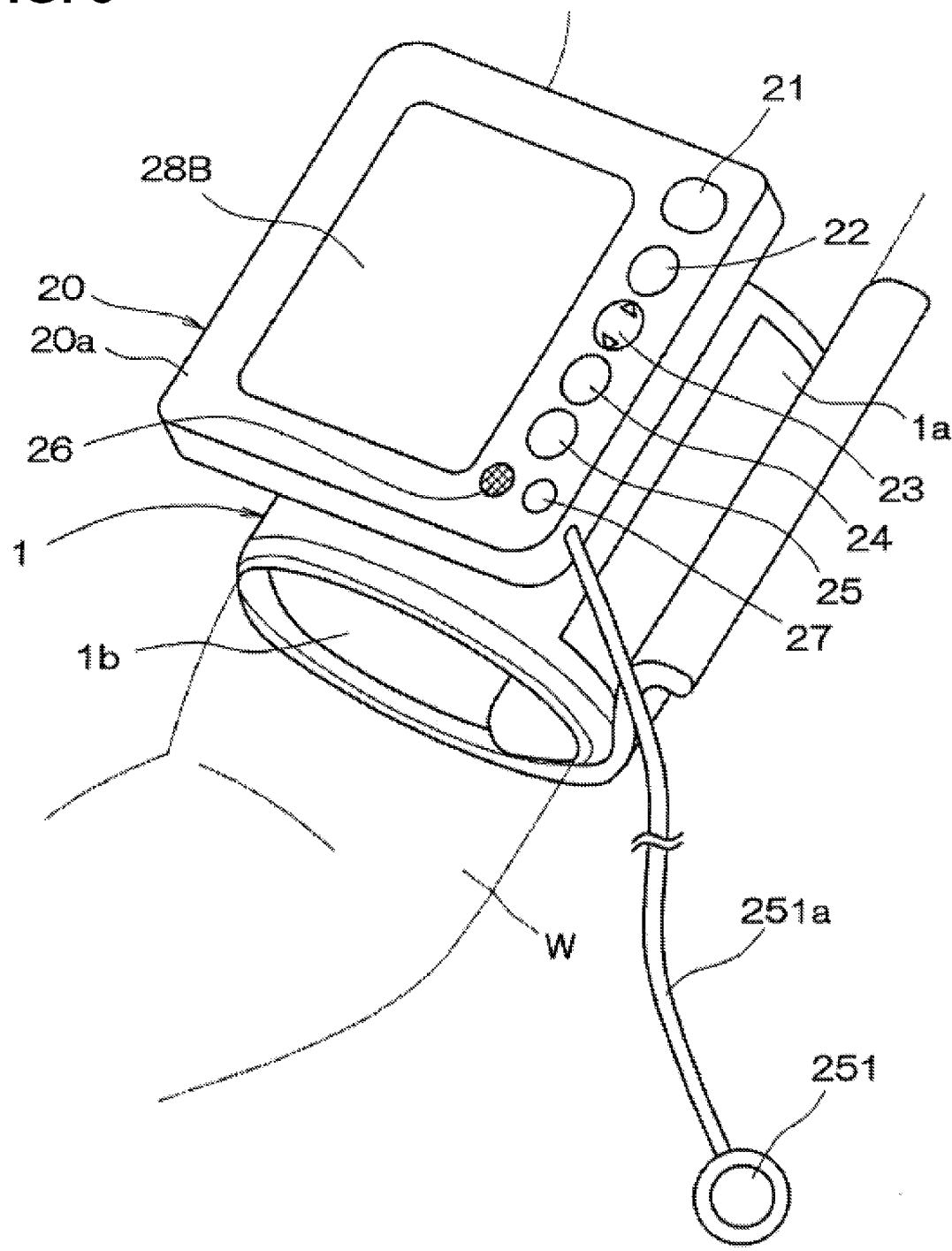
FIG. 5 is a perspective diagram which shows the appearance of a simple automatic electronic tourniquet shown as the third embodiment of the present invention.
Figure 6:
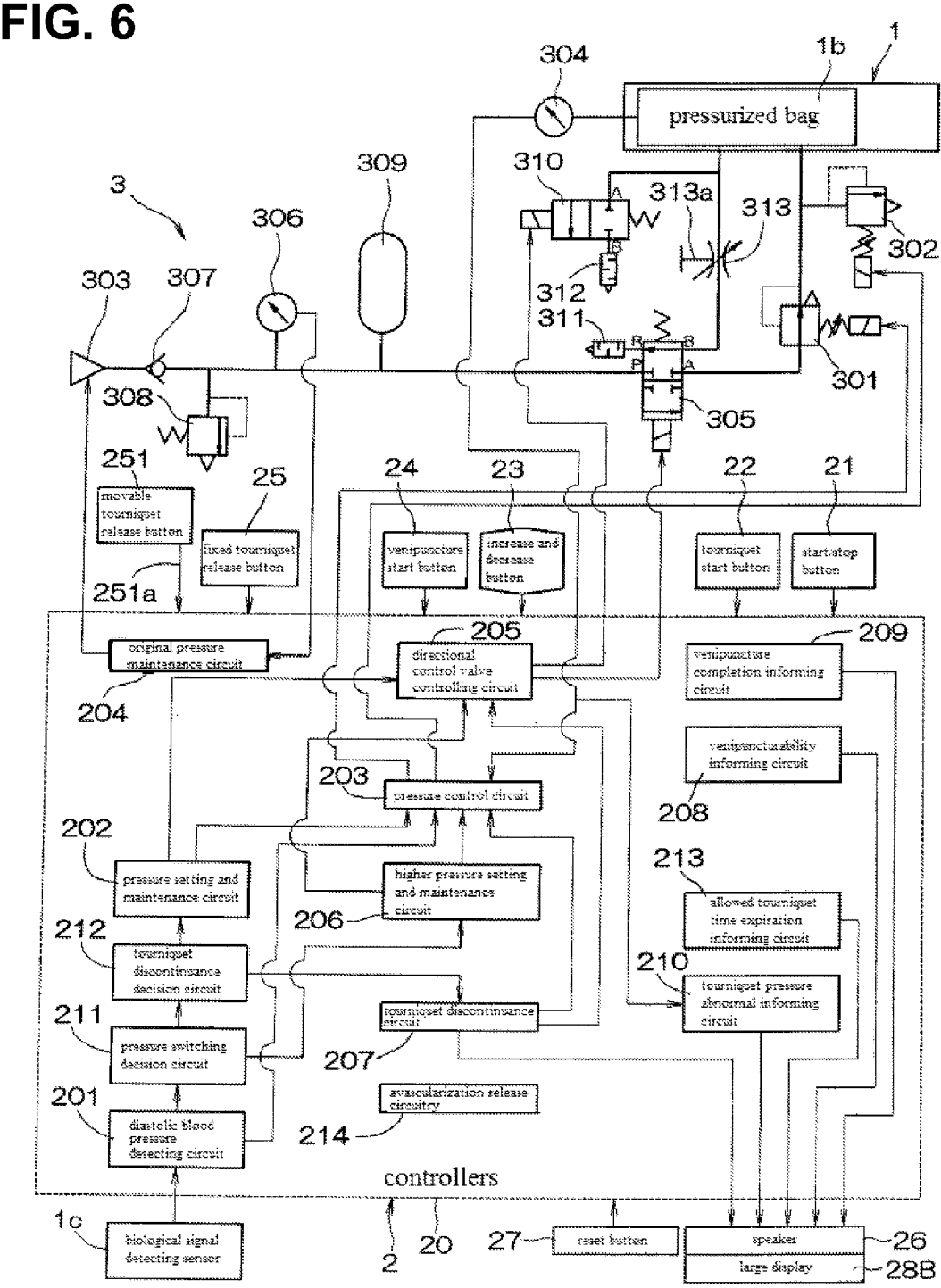
FIG. 6 is a block diagram which shows the controllers in a simple automatic electronic tourniquet shown as the third embodiment of the present invention.

Then, the third embodiment of the present invention is described with reference to FIGS. 5 and 6. However, the same code is referred to elements common to the elements of the second embodiment shown in FIGS. 3 and 4, and explanations thereon are omitted.

The difference between the third embodiment of the simple automatic electronic tourniquet and the second embodiment is that a large display 28B is provided as informing means, that the fixed throttle 305a is removed in the directional control valve 305, and that a variable throttle (variable flow regulating valve) 313 is provided between the pressurized bag 1b and the B port of the directional control valve 305.

Since the fixed throttle 305a is removed from the directional control valve 305, the R port is simply communicated with the R port in the neutral position. The variable throttle 313 can adjust, by a rotary knob 313a, rate of flow of the air discharged from the pressurized bag 1b to the atmosphere through the B port of the directional control valve 305, R port and the muffler 311.

The display 28B displays information content and can display simultaneously data on tourniquets such as target pressures, maximum pressures, minimum pressures, higher target pressures, higher maximum pressures, higher minimum pressures, and pressures of the pressurized bag 1b.

In the simple automatic electronic tourniquet configured as above-described, when pressures of the pressurized bag 1b are decreased by the diastolic blood pressure detecting circuit 201, the pressure setting and maintenance circuit 202, the higher pressure setting and maintenance circuit 206, and so on, the air supply from the air pump 303 to the pressurized bag 1b is suspended by maintaining the exhaust directional control valve 310 in the neutral position through the directional control valve controlling circuit 205 and by returning the directional control valve 305 to the neutral position, and the pressurized bag 1b is also made open to the atmosphere through variable throttle 313, directional control valve 305 and the muffler 311. Thereby, at the rate of airflow restricted by the variable throttle 313, pressures of the pressurized bag 1b can be decreased.

In this case, since the air flow passing through the variable throttle 313 can be adjusted by turning rotary knob 313a, time before reaching minimum pressures from maximum pressures can be set freely within a predetermined range. Note that in this case, if the decreasing speed of pressures of pressurized bag 1b is controlled only by the variable throttle 313, the relief valve 302 can be omitted.

Note that each embodiment of the present invention is configured to control pressures to the upper arm W by the manchette 1 by means of pressures of the air of the pressurized bag 1b provided on the manchette 1. However, it may be configured to control the pressures by such as adjusting the length of the manchette 1 in its circumferential direction. In this case, the control is performed in the same manner as in the case of using the pneumatic equipment 3. For example, pressures of the manchette 1 is controlled so as to correspond to such as the diastolic blood pressure by controlling wind-up quantity of the manchette 1 with driving means such as an electric motor.

Also, in each of the above-described embodiments, an example is shown in which the wrapping member is configured with the manchette 1. However, the wrapping member may be configured to be simply formed in a cylindrical shape into which each extremity such as the arm is insertable, and to be provided pressure-applying means such as the pressurized bag 1b along its internal surface.

Furthermore, as the controller 2, the one is shown which is provided with the electronic device using the hardware resources with the computer and is configured with so-called programmable logic controller (PLC) in which sequence control circuits can be constructed with programs. However, another one may be included in which the sequence control circuits can be constructed with electronic circuits such as static relays.

DENOTATION OF REFERENCE NUMERALS 1 manchette (wrapping member)
1c biological signal detecting sensor
2 controllers
3 pneumatic equipment
20 casing
25 fixed tourniquet release buttons (tourniquet release button)
26 speakers (informing means)
28A small display (informing means)
28B large display (informing means)
201 diastolic blood pressure detecting circuit
202 pressure setting and maintenance circuit
206 higher pressure setting and maintenance circuit
207 tourniquet discontinuance circuit
208 venipuncturability informing circuit
210 tourniquet pressure abnormal informing circuit
211 pressure switching decision circuit
212 tourniquet discontinuance decision circuit
213 allowed tourniquet time expiration informing circuit
214 avascularization release circuitry
251 movable tourniquet release buttons (tourniquet release button)
301 reducing valve (pressure control valve)
302 relief valve (pressure control valve)
303 air pump
304 pressure sensor
305a fixed throttle (flow regulating valve)
313 variable throttle (flow regulating valve)
W upper arm

The invention claimed is:

1. A simple auto electronic tourniquet comprising:
a wrapping member configured to wrap around an extremity of a human body and a controller provided on the wrapping member and configured to control pressure applied to the extremity by the wrapping member;
the controller comprising a diastolic blood pressure detecting circuit and a pressure setting and maintenance circuit;
the diastolic blood pressure detecting circuit configured to detect a development of a biological signal concerning a diastolic blood pressure occurring in the extremity when a pressure within the wrapping member is increased;
the pressure setting and maintenance circuit configured to set a first target pressure corresponding to the pressure within the wrapping member when the development of the biological signal is detected by the diastolic blood pressure detecting circuit and configured to control the pressure applied by the wrapping member to fall within a range of the target pressure.

2. The simple auto electronic tourniquet according to claim 1, wherein the diastolic blood pressure detecting circuit is further configured to detect a disappearance of the biological signal concerning the diastolic blood pressure occurring in the extremity when the pressure within the wrapping member is decreased;
the pressure setting and maintenance circuit is further configured to set a second target pressure corresponding to the pressure within the wrapping member when the disappearance of the biological signal is detected by the diastolic blood pressure detecting circuit;
the pressure setting and maintenance circuit is further configured to set a maximum pressure corresponding to a first value equal to the first target pressure increased by a first predetermined allowable pressure and to set a minimum pressure corresponding to a second value equal to the second target pressure reduced by a predetermined allowable pressure of more than 0 (zero); and
the pressure setting and maintenance circuit is configured to reset the first and second target pressures, the maximum pressure and the minimum pressure depending on changes of the diastolic blood pressure.

3. The simple auto electronic tourniquet according to claim 2, wherein the controller further comprises a tourniquet pressure abnormal informing circuit configured to detect the pressure within the wrapping member and to send a signal to an output informing of abnormal tourniquet pressure when the pressure within the wrapping member is higher than the maximum pressure or lower than the minimum pressure.

4. The simple auto electronic tourniquet according to claim 2, wherein the controller further comprises a tourniquet discontinuance decision circuit configured to shift to a tourniquet discontinuance circuit when the development or the disappearance of the biological signal cannot be detected by the diastolic blood pressure detecting circuit until the pressure within the wrapping member reaches a predetermined pressure; and
wherein the tourniquet discontinuance circuit is configured to control a decrease in pressure within the wrapping member and to output a signal informing of tourniquet discontinuance.

5. The simple auto electronic tourniquet according to claim 1, wherein the controller further comprises a venipuncturability informing circuit configured to send a signal to an output that venipuncture can begin after a predetermined time from the setting of a first target pressure.

6. The simple auto electronic tourniquet according to claim 1, wherein the controller further comprises an allowed tourniquet time expiration informing circuit configured to measure tourniquet times from the setting of the first target pressure and to send output signals informing that the tourniquet times have reached an end of predetermined allowable tourniquet times.

7. The simple auto electronic tourniquet according to claim 1, wherein the controller further comprises a tourniquet release circuit configured to reduce the pressure within the wrapping member based on a signal emitted from a tourniquet release button; and
wherein the tourniquet release button is provided on a casing which covers the controller or is moveable, and emits the signal to the tourniquet release circuit.

8. The simple auto electronic tourniquet according to claim 1, wherein the wrapping member comprises an air pump, a pressure control valve, a pressure sensor and a biological signal detecting sensor;
wherein the air pump is configured to supply a source of compressed air to the wrapping member;
wherein the pressure control valve is configured to adjust the pressure within the wrapping member by adjusting pressure of air supplied from the air pump based on a command from the controller;
wherein the pressure sensor is configured to detect the pressure within the wrapping member based on the pressure of air within the wrapping member; and
wherein the biological signal detecting sensor is configured to detect the biological signal.

9. The simple auto electronic tourniquet according to claim 8, further comprising a fixed or variable flow-regulating valve configured to adjust a decreasing speed of the pressure within the wrapping member by limiting a rate of flow of air discharged from the wrapping member.

* * * * *